US00PP23370P2

(12) United States Plant Patent
Delabroye

(10) Patent No.: US PP23,370 P2
(45) Date of Patent: Jan. 29, 2013

(54) ***GERANIUM* PLANT NAMED 'CATHERINE DENEUVE'**

(50) Latin Name: *Geranium* hybrid
Varietal Denomination: Catherine Deneuve

(76) Inventor: Sandrine Delabroye, Hantay (FR)

( * ) Notice: Subject to any disclaimer, the term of this patent is extended or adjusted under 35 U.S.C. 154(b) by 8 days.

(21) Appl. No.: 13/199,187

(22) Filed: Aug. 22, 2011

(51) Int. Cl.
*A01H 5/00* (2006.01)

(52) U.S. Cl. ..... Plt./324

(58) Field of Classification Search ..... Plt./324
See application file for complete search history.

*Primary Examiner* — Kent L Bell
(74) *Attorney, Agent, or Firm* — Penny J. Aguirre

(57) ABSTRACT

A new cultivar of hybrid *Geranium*, 'Catherine Deneuve', characterized by its very long bloom season, blooming from the end of May into September in the Netherlands, its star-shaped flowers that are deep magenta-pink in color, and its very vigorous growth habit.

2 Drawing Sheets

Botanical classification: *Geranium* hybrid.
Cultivar designation: 'Catherine Deneuve'.

BACKGROUND OF THE INVENTION

The present invention relates to a new and distinct cultivar of *Geranium* plant, botanically of hybrid origin and known as *Geranium* 'Catherine Deneuve' and will be referred to hereafter by its cultivar name, 'Catherine Deneuve'.

'Catherine Deneuve' was discovered as a chance seedling in a trial garden by the Inventor in Hantay, France in 2009. The exact parentage is unknown, but 'Catherine Deneuve' is believed to be an interspecific cross between plants of *Geranium psilostemon* and *Geranium procurrans* based on the characteristic of the new cultivar and their proximity to the discovered seedling.

Asexual reproduction of the new cultivar was first accomplished by in vitro propagation under the direction of the Inventor in Rijswijk, The Netherlands in 2010. Propagation by tissue culture and division has determined that the characteristics of this cultivar are stable and are reproduced true to type in successive generations.

SUMMARY OF THE INVENTION

The following traits have been repeatedly observed and represent the characteristics of 'Catherine Deneuve'. These attributes in combination distinguish 'Catherine Deneuve' as a new and distinct cultivar of *Geranium*.

1. 'Catherine Deneuve' exhibits a very long bloom season, blooming from the end of May into September in the Netherlands.
2. 'Catherine Deneuve' exhibits star-shaped flowers that are deep magenta-pink in color.
3. 'Catherine Deneuve' exhibits a very vigorous growth habit.

'Catherine Deneuve' can be compared to plants of its probable parent species. Plants of *Geranium psilostemon* differ from 'Catherine Deneuve' in being much taller in height, in having flowers that are more rounded and lighter purple-pink in color, and in having a shorter bloom period. Plants of *Geranium procurrans* differ from 'Catherine Deneuve' in having flowers that are rounder in shape and purple in color with dark purple veins and in commencing bloom later in the season. 'Catherine Deneuve' can be most closely compared to the cultivar 'Ann Folkard' (not patented), as it is also a *G. psilostemon*×*G. procurrans* hybrid. 'Ann Folkard' is similar to 'Catherine Deneuve' in flower color and in being long blooming, however 'Ann Folkard' differs from 'Catherine Deneuve' in having rounder shaped flowers and in having new leaves that are yellow in color.

BRIEF DESCRIPTION OF THE DRAWING

The accompanying colored photographs illustrate the overall appearance and distinct characteristics of the new *Geranium*. The photographs were taken of an 18 month-old plant of 'Catherine Deneuve' as grown outdoors in a 19-cm container in The Netherlands.

The photograph in FIG. 1 is a side view of a plant of 'Catherine Deneuve' in bloom.

Figure 1:
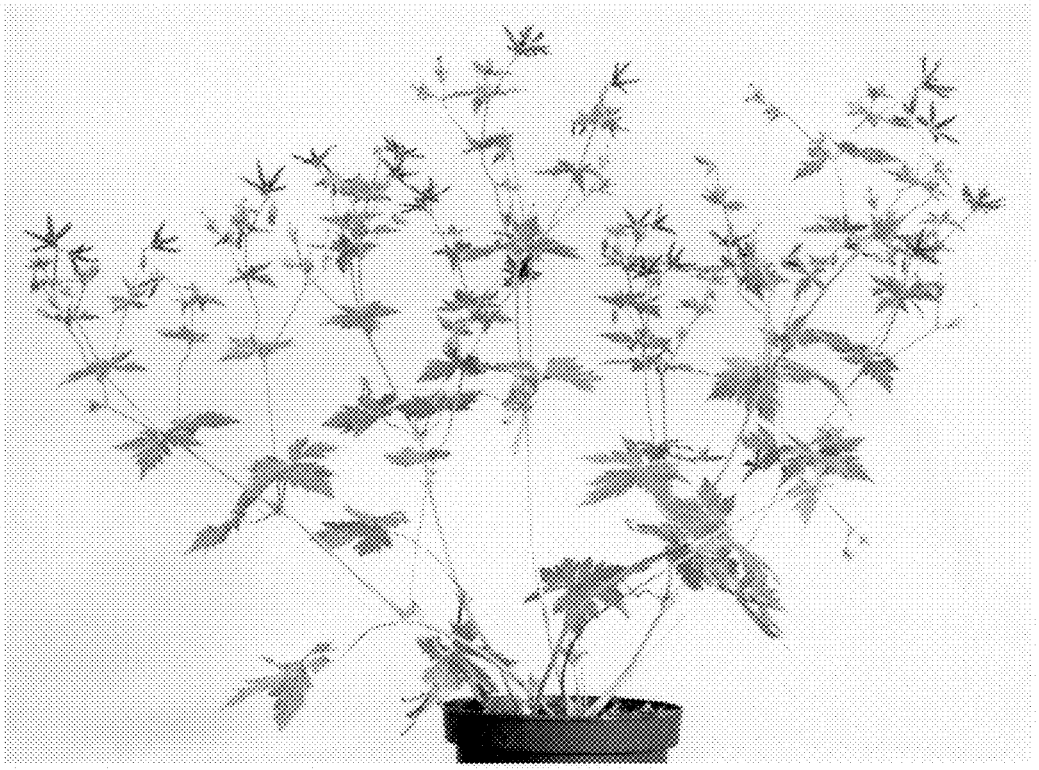
Figure 2:
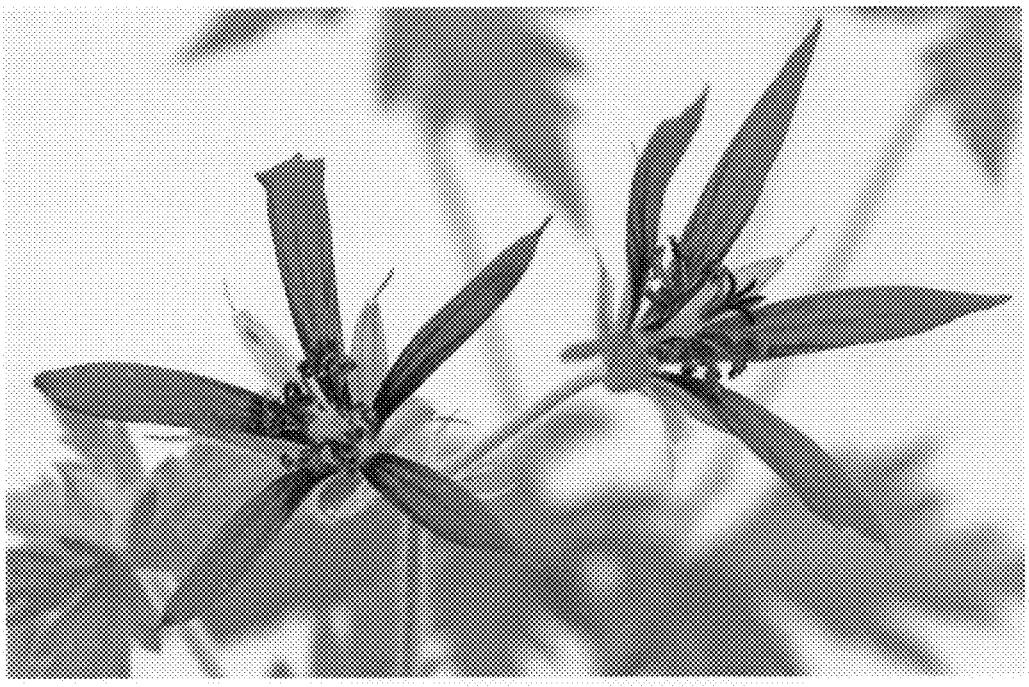
Figure 3:
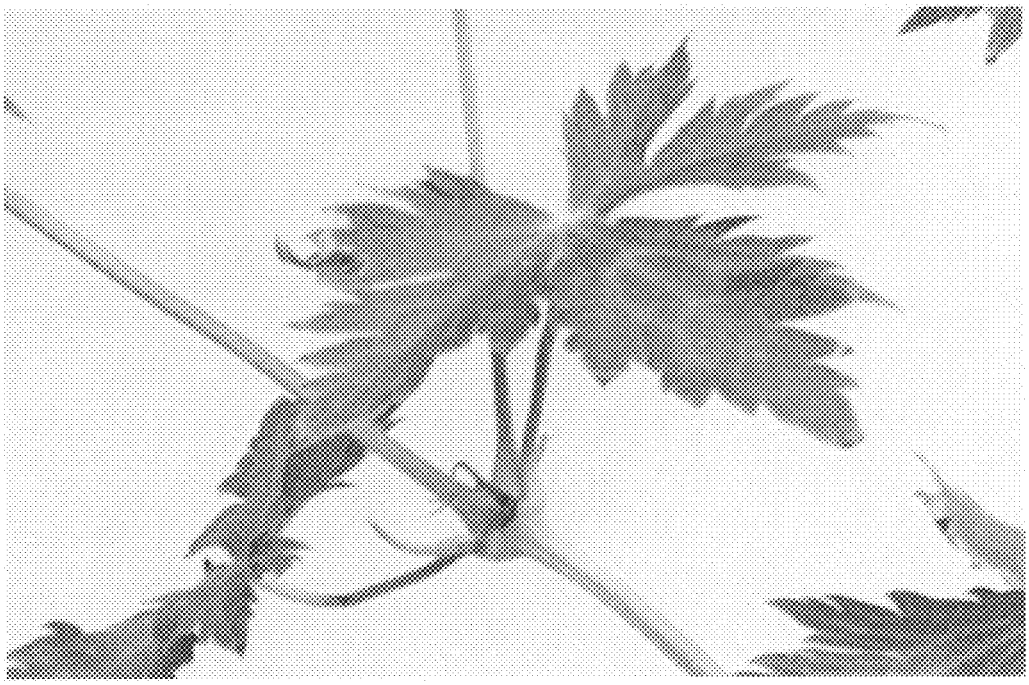

The photograph in FIG. 2 is of a close-up view of two flowers of 'Catherine Deneuve' and the photograph in FIG. 3 provides a close-up view of a leaf of 'Catherine Deneuve'. The colors in the photograph may differ slightly from the color values cited in the detailed botanical description, which accurately describe the colors of the new *Geranium*.

DETAILED BOTANICAL DESCRIPTION OF THE PLANT

The following is a detailed description of 18 month-old plants of the new cultivar as grown outdoors in 19-cm containers in Warmond, The Netherlands with average day temperatures of 15° C. to 28° C. and average night temperatures of 6° C. to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—End of May into September in The Netherlands.

*Plant habit*.—Herbaceous perennial with broad spreading upright growth habit.

*Height and spread*.—Reaches 50 cm in height and about 70 cm in spread.

*Cold hardiness*.—At least to U.S.D.A. Zone 5.

*Heat tolerance*.—At least tolerant to temperature up to 35° C.

*Diseases and pests*.—No particular resistance or susceptibility in comparison to other cultivars of *Geranium*.

*Root description*.—Fleshy roots extending from stout rootstock.

Growth and propagation:

*Growth rate*.—Vigorous, about 15 cm per month in spring.

*Propagation*.—Division and In vitro propagation.

Stem description:

*Stem size*.—Average of 52.4 cm in length and 3.5 mm in width.

*Stem shape*.—Slightly angled.

*Stem color*.—180A, under side; 144A to 144B (without sun exposure).

*Stem surface*.—Slightly glossy, young stems densely covered with soft hairs; average of 1 mm in length, 155C in color.

*Internode length*.—Average of 13.5 cm.

*Branching*.—Moderately branching with an average of 6 lateral branches.

Foliage description:

*Leaf shape*.—Orbicular (overall shape), palmately cleft with an average of three lobes (occasionally five-lobed).

*Leaf division*.—Simple.

*Leaf base*.—Hastate (not overlapping).

*Leaf apex*.—Acute.

*Leaf venation*.—Palmate, 144B in color on upper surface and 145C to 145D on lower surface.

*Leaf margins*.—Palmately cleft, lobes serrate, average of 3 lobes, occasionally 5.

*Leaf attachment*.—Petiolate.

*Leaf arrangement*.—Opposite.

*Leaf surface*.—Upper surface moderately covered in very short soft hairs, lower surface densely covered with very short soft hairs, especially on main and secondary veins; average of 0.8 mm in length, 157D in color.

*Leaf color*.—Young leaves upper surface; 143A, young leaves lower surface;138B, mature leaves upper surface; 137B, mature leaves lower surface; 146B.

*Leaf size*.—Average of 7.4 cm in length and 9.2 cm in width.

*Leaf quantity*.—Average of 8 leaves per lateral branch.

*Petioles*.—Average of 6 cm length and 2 mm in width, color; a blend of 176A to 176C, underside; 144D in color.

*Stipules*.—A leafy stipule is present on both sides of the base of each leaf, shaped lanceolate, 1.4 cm in length and 3 mm in width, color of both sides; 181C, base 145B, older stipules dry but persistent, 199B in color.

Flower description:

*Inflorescence type*.—Single, rotate flowers, arranged in pairs of 2.

*Lastingness of flowers*.—About 7 days.

*Flower size*.—Average of 1.3 cm in height and 4.2 cm in diameter.

*Flower fragrance*.—None.

*Flower number*.—Average of 10 per lateral branch, continuously producing blooms.

*Flower aspect*.—Upright to slightly outward.

*Flower buds*.—Narrowly ovate in shape, average of 1.5 cm in length and up to 6 mm in width, color; 138A, veins; 137B to 137C, densely covered with short glandular hairs, average length 1 mm, color; NN155D.

*Petal number*.—5.

*Petal shape*.—Obcordate.

*Petal color*.—Opening upper surface; N74A, base and veins; N79 becoming a blend of N79A and 187A, opening lower surface; 71B, fully opened upper surface; 72A, base and veins; a blend of N79A and 187A, fully open lower surface; 71B.

*Petal surface*.—Velvety and dull on upper surface, slightly glossy on lower surface.

*Petal margins*.—Entire to irregularly incised with an average of 2 incisions.

*Petal apex*.—Acute.

*Petal size*.—Average of 2.2 cm in length and 6 mm in width.

*Calyx form*.—Rotate, strongly cupped, 9 mm in length, 2.6 cm in diameter.

*Sepals*.—5, rotate arrangement, lanceolate to oblong in shape, average of 1.5 mm length and 3 mm in width, entire margin, mucronate apex, cuneate base, upper and lower surface is dull and glabrous, color; young upper surface; 143C, veins; 137B to 137C, mature upper surface; 143B to 143C, veins; 137B to 137C, young lower surface; 138A, veins; 137B to 137C, mature lower surface; 138A, veins; 137B to 137C.

*Peduncles*.—Round in shape, average of 4 cm in length and 1 mm in diameter, moderately strong, held at about a 35° angle relative to lateral branch, color; 177B, lower surface; a blend of 144C and 145B, pubescent surface.

*Pedicels*.—Round in shape, average of 1.8 cm in length and 1 mm in diameter, moderately strong, held at about a 15° angle relative to peduncle on lateral flowers, color; 138B to 138C, pubescent surface.

Reproductive organs:

*Gynoecium*.—1 pistil, about 4 mm in length, 5 stigmas are decurrent and 202A in color, style is about 2 mm in length, N186D in color, ovary is 138C to 138D in color.

*Androecium*.—10 stamens, anthers are dorsifixed, oblong and winged in shape, 2 mm in length, 71B in color, filaments are 6 mm in length and 71A in color, pollen is very low in quantity and 160A to 160B in color.

*Fruit/seeds*.—None observed.

It is claimed:

1. A new and distinct cultivar of *Geranium* plant named 'Catherine Deneuve' as herein illustrated and described.

* * * * *